(12) United States Patent
Israelowitz et al.

(10) Patent No.: US 9,222,074 B2
(45) Date of Patent: Dec. 29, 2015

(54) PROCESS FOR PRODUCING THREE-DIMENSIONAL TISSUE (75) Inventors: Meir Israelowitz, Toronto (CA); Birgit Weyand, Hannover (DE); Peter Vogt, Hannover (DE); Kerstin Reimers, Hannover (DE); Herbert von Schroeder, Toronto (CA); Christoph Gille, Toronto (CA); Elmar Schmaelzlin, Postdam (DE)

(73) Assignees: Medizinische Hochschule Hannover, Hannover (DE); Biomimetics Technologies, Inc., Toronto (CA); Marvin Stolz, Berlin (DE); Dr. Elmar Schmaelzlin, Postdam (DE)

( * ) Notice: Subject to any disclaimer, the term of this patent is extended or adjusted under 35 U.S.C. 154(b) by 51 days.

(21) Appl. No.: 13/877,575

(22) PCT Filed: Oct. 4, 2011

(86) PCT No.: PCT/EP2011/067344
§ 371 (c)(1),
(2), (4) Date: Jul. 8, 2013

(87) PCT Pub. No.: WO2012/045756
PCT Pub. Date: Apr. 12, 2012

(65) Prior Publication Data
US 2013/0337433 A1 Dec. 19, 2013

Related U.S. Application Data (60) Provisional application No. 61/404,320, filed on Oct. 4, 2010.

(51) Int. Cl.
*C12Q 3/00* (2006.01)
*G01N 33/84* (2006.01)
(Continued)

(52) U.S. Cl.
CPC ............ *C12N 5/0675* (2013.01); *C12N 5/0062* (2013.01); *C12N 5/0662* (2013.01);
(Continued)

(58) Field of Classification Search
None
See application file for complete search history.

(56) References Cited

U.S. PATENT DOCUMENTS

2004/0171094 A1 9/2004 Klimant et al.
2005/0058842 A1 3/2005 Liebmann-Vinson et al.

FOREIGN PATENT DOCUMENTS

EP 2031501 3/2009

OTHER PUBLICATIONS

Elmar Schmälzlin, Joost T. van Dongen, Ingo Klimant, Bettina Marmodée, Martin Steup, Joachim Fisahn, Peter Geigenberger, and Hans-Gerd Löhmannsröben, An Optical Multifrequency Phase-Modulation Method Using Microbeads for Measuring Intracellular Oxygen Concentrations in Plants, 2005, Biophysical Journal, vol. 89, pp. 1339-1345.*

(Continued)

*Primary Examiner* — Ralph Gitomer
*Assistant Examiner* — Trent Clarke
(74) *Attorney, Agent, or Firm* — Greer, Burns & Crain, Ltd.

(57) ABSTRACT

The invention provides a process for producing a three-dimensional tissue by cultivating eucaryotic cells by introducing the cells into a matrix and cultivating the cells within the matrix in a cell culture medium within a cell culture vessel under controlled dissolved oxygen conditions of the cell culture medium. The matrix contains a support containing an optical oxygen sensor, which is an oxygen-sensitive dye, which upon irradiation with an excitation wavelength changes its emission characteristics in dependence on the dissolved oxygen concentration in the surrounding medium, including a dye phosphorescing upon irradiation of an excitation wavelength, which phosphorescence is quenched by dissolved oxygen.

14 Claims, 4 Drawing Sheets (51) Int. Cl.
C12N 5/0775 (2010.01)
C12N 5/00 (2006.01)

(52) U.S. Cl.
CPC ............ *C12N5/0663* (2013.01); *C12N 5/0664* (2013.01); *C12N 5/0665* (2013.01); *C12N 5/0666* (2013.01); *C12N 5/0667* (2013.01); *C12N 5/0668* (2013.01); *C12Q 3/00* (2013.01); *G01N 33/84* (2013.01); *C12N 2500/02* (2013.01)

(56) References Cited

OTHER PUBLICATIONS

Stephanie J. Bryant, Jeffrey A. Arthur, Kristi S. Anseth, Incorporation of tissue-specific molecules alters chondrocyte metabolism and gene expression in photocrosslinked hydrogels, 2005, Acta Biomaterialia, vol. 1, pp. 243-252.*

Kyung Hwan Lee, Gum Ju Sun, and Kyu Ho Chae, Photografting of Polystyrene: III. Preparation of Chemically Modified Polystyrene Containing Oxime-Ester Groups and its Photografting with Hydroxyethyl Methacrylate, 2000, Journal of Photoscience, vol. 7(4), pp. 149-152.*

Acosta, Miuel A ., "Fluorescent microparticles for sensing cell microenvironment oxygen levels within 3D scaffolds", *Biomaterials*, 30, (2009), 3068-3074.

Schmaelzlin, Elmer, et. al., "Monitoring hormone-induced oxygen consumption in the salivary glands of the blowfly, *Calliphora vicina*, by use of luminescent microbeads", *Sensor and Actuators B*, (2006), 251-2354.

Thomas, Peter C., et. al., "A Noninvasive Thin Film Sensor for Monitoring Oxygen Tension during in Vitro Cell Culture", *Anal. Chem.*, 2009, 81, 9239-9246.

* cited by examiner

PROCESS FOR PRODUCING THREE-DIMENSIONAL TISSUE

The present invention relates to a process for producing a three-dimensional tissue using cultivation of eucaryotic cells, e.g. plant or animal cells, preferably human cells within a matrix material, especially for producing a transplant. The matrix, also referred to as a scaffold, can be permeated by components of the cultivation medium, e.g. by permeation and/or diffusion, and can be a porous, permeable matrix, e.g. a gel or a non-swellable matrix. The process provides for an optical measurement of the dissolved oxygen concentration within the matrix, and preferably the control of the composition and/or the flow of cultivation medium in dependence on the measurement signal representing the dissolved oxygen concentration.

Further, the invention relates to the cultivated tissue comprising the matrix, e.g. obtainable by the process of the invention, the tissue and matrix comprising a portion of the dissolved oxygen measurement device, and relates to the use of the cultivated tissue comprising the matrix for use as a tissue implant for medical purposes, e.g. as an implant for filling tissue defects.

STATE OF THE ART

Schmälzlin et al in Sensors and Actuators B, 251-254 (2006) describe the introduction of polystyrene beads containing Pt(II)-tetra pentafluorophenyl-porphyrin into isolated salivary gland tissue of the blowfly and irradiating the tissue at 509 nm and detecting the phase shift of phosphorescence for determining the dissolved oxygen concentration within the tissue.

EP 2 031 501 A2 describes a bio-reactor containing a grid serving as a carrier for supporting a biomaterial, wherein the grid has openings allowing a laminar flow of cultivation medium adjacent the biomaterial.

OBJECTS OF THE INVENTION

It is an object to provide an improved production process for producing a three-dimensional tissue, especially with an alternative measurement of the dissolved oxygen concentration, and preferably with an improved control of cultivation conditions.

GENERAL DESCRIPTION OF THE INVENTION

The invention achieves the above-mentioned objects by the features of the claims, especially by providing a process for producing a three-dimensional tissue by cultivating eucaryotic cells, e.g. plant or animal cells, preferably human cells, especially adherently growing cells, more preferably human adherently growing cells, e.g. human mesenchymal stem cells, by introducing the cells into a matrix and cultivating the cells within the matrix in a cell culture medium within a cell culture vessel under controlled dissolved oxygen conditions of the cell culture medium. Preferably, the matrix is a material swellable in the cell culture medium, e.g. a three-dimensional collagen, or a non-swellable material.

A three-dimensional tissue preferably has at least 5, more preferably at least 20 cell layers thickness, more preferably, the matrix and the three-dimensional tissue containing the matrix as produced by the process has a minimum thickness or minimum cross-section of at least 0.2 mm, preferably of at least 0.5 mm, more preferably of at least 1 mm or of at least 2 mm or 5 mm, more preferred of at least 10 or at least 20 mm.

According to the invention, the matrix contains a support containing an optical oxygen sensor, which is an oxygen-sensitive dye, which upon irradiation with an excitation wavelength changes its emission characteristics in dependence on the dissolved oxygen concentration in the surrounding medium, including a dye phosphorescing upon irradiation of an excitation wavelength, which phosphorescence is quenched by dissolved oxygen. The support is oxygen-permeable, e.g. permeable to diffusion by oxygen into the support, and contains the oxygen-sensitive dye within its inner volume, e.g. the dye is contained in interstices of the support and/or impregnated and/or incorporated into the support material, e.g. by diffusion into the support. An oxygen-sensitive dye for use in the invention can e.g. be a metal-containing porphyrin compound, a Ru-containing complex of phenanthronline and/or of bisphenyl, tris(4,7-diphenyl-1,10-phenanthroline)ruthenium II having absorption and emission maxima at approx. 450 and 590 nm, respectively, metal-containing benzoporphyrins or metal-containing azatetrabenzoporphyrins, which can be excited at a wavelength of approx. 610 nm, emitting in the near infrared range. Optionally, the complex can have halogenated ligands, e.g fluorinated ligands, for improving photostability. A preferred example for a dissolved oxygen sensitive dye has the absorption and emission characteristics of Pt(II)-tetra-pentafluorophenyl-porphyrin, and most preferred, the dye is Pt(II)-tetra-pentafluorophenyl-porphyrin. The excitation wavelength preferably is 500-570 nm, preferably 510-532 nm, more preferably 510-515 nm. An excitation wavelength of 510-532 nm is preferred, because a cell culture medium is essentially optically transparent for this wavelength, and the preferred oxygen sensitive dye has two local absorption maxima. For producing the excitation wavelength, an LED and/or a laser can be used. For detecting the emission characteristics, e.g. the time-resolved intensity of radiation emitted by the dissolved oxygen sensitive dye, an optical detector, preferably a photomultiplier, is directed to the matrix. The emission is preferably analysed for a narrow frequency range which is pre-set, e.g. pre-set to the frequency in which the excitation wavelength is modulated. Preferably, the emission is determined in a pre-set frequency range using a lock-in amplifier.

In accordance with the optical nature of the measurement method, it is preferred that the matrix is optically translucent for both the excitation wavelength and for the emission wavelength of the dye contained in the support.

Preferably, the excitation wavelength is sinusoidal irradiation, more preferably sinusoidal irradiation simultaneously modulated to two different frequencies, e.g. modulated to approx. 6 kHz and approx. 11 kHz for Pt(II)-tetra-pentafluorophenyl-porphyrin. Detection comprises the detection of the time-dependent intensity of light emission following the irradiation of excitation wavelengths, e.g. detection of the time-dependent intensity of light emission following the modulated irradiation emitted from the phosphorescent dye, preferably the detection of the phase shift for each frequency of the modulated excitation irradiation. Measurement of each of the phase shifts at two different modulation frequencies allows quantification while masking residual excitation irradiation and of non-specific background fluorescence, which may originate from cells, from the matrix and from the culture medium. From the determined phase shifts, the decay time of the dye is calculated. Using a calibration relation previously determined for the decay times for known dissolved oxygen concentrations of the support containing the dye, preferably with the support containing the dye being immobilized within the matrix, the current phase shift signals can be converted into current dissolved oxygen concentrations. Preferably, the conversion of the signals indicating the dissolved oxygen concentration is made with correlation to the temperature of the matrix and/or medium within the vessel and/or with correlation to the pressure within the vessel, preferably using the temperature-dependent signal of a temperature sensor and/or a pressure-dependent signal, e.g. at one or two pressure-ports arranged at the vessel, e.g. by the computer used for determining the phase shift. Accordingly, it is preferred to predetermine a temperature-dependent and/or pressure-dependent calibration curve of the correlation of the phase-shift signal and the dissolved-oxygen concentration, preferably at the cultivation temperature to which the medium is controlled.

This dye, which is sensitive to dissolved oxygen, is contained in a soluble and/or particulate support which is permeable for oxygen. The support can be a scaffold in which the dye is e.g. entrapped or encapsulated. The support containing the dye can contain or consist of polystyrene, polymethylmethacrylate, polyethylene, polypropylene, ormosile, silicone, sol-gel matrices, compounds having a dendrimer structure, blends of these polymers and/or of their halogenated derivatives and mixtures thereof. The support causes a great enhancement of the phosphorescence intensity, and reduces cross sensitivities or non-specific phosphorescence. In the presence of oxygen, dissolved or gaseous, the phosphorescence of the dye contained in the support is quenched in a concentration-dependent manner. Preferably, the support is particulate having e.g. a diameter in the range of 0.03-200 μm, preferably 1-100 μm, more preferably 10-70 μm, even more preferably 40-60 μm, e.g. approx. 50 μm. The support containing the oxygen-sensitive dye is integrated into the matrix, especially for a water-swellable matrix material, by mixing the dye which is coupled to a particulate or soluble support, with the matrix material, followed by forming the mixture of the matrix material with the dye contained in the support, e.g. into a shape suitable for positioning into a cultivation vessel and/or into a shape desired for the tissue to be produced.

The dissolved-oxygen sensitive dye is preferably immobilized within the matrix, especially by coupling of the particulate or soluble support containing the dye to the matrix, e.g. by arrangement of the support containing the dye in interstices of the matrix, and/or by chemically coupling the support containing the dye to the matrix. The immobilization of the support containing the oxygen-sensitive dye to the matrix allows the optical measurement of the oxygen concentration within the immediate vicinity of the cells growing in the matrix with a reduced loss of dye from the matrix, e.g. due to wash-out.

For coupling the support containing the dye to the matrix, one or both of the components to be coupled, i.e. the support and/or the matrix can be provided with a chemically reactive group. As a chemically reactive group, an amine group, a carboxyl group, carboxylate group, an ethylenically unsaturated group, e.g. a (meth)acrylic group can be coupled to the matrix and/or to the support; preferably both the compounds to be coupled are derivatized by introducing a chemically reactive group and reacted to form a chemical bond between the reactive groups.

Additionally or in the alternative, for coupling support containing the dye to the matrix, the support containing the dye can be provided in an admixture with a polymerizable compound in contact with the matrix, followed by initiating polymerization, e.g. by adding a starter compound. Preferably, both the polymerizable compound and the starter compound are pharmaceutically acceptable compounds. A preferred example for a polymerizable compound is fibrinogen, and the starter compound is plasminogen or thrombin, resulting e.g. in the immobilisation of the support containing the dye in the matrix in combination with a fibrin polymer.

The immobilization of the support containing the dye, which in the invention is a dissolved oxygen sensitive dye having a phosphorescence that depends on the dissolved oxygen concentration in the surrounding medium within the matrix, has the advantage of allowing a contactless, i.e. optical measurement of the dissolved oxygen concentration in the immediate surroundings of the cells growing in the matrix, without introducing the dye or the support into the cells. As the support containing the dye can be immobilized homogeneously within the volume of the matrix, and because the excitation wavelength and the emission can at least partially cross a volume portion of the matrix, a precise measurement of the dissolved oxygen concentration within the inner volume of the matrix can be performed.

In order to reduce the influence of the oxygen measurement device on the preferred laminar flow within a cultivation vessel, it is preferred that both the light source irradiating the excitation wavelength and the detector receiving the emission from the dye are arranged within the wall of the cultivation vessel, and most preferably the light source and the detector surface are flush with the inner surface of the cultivation vessel.

For controlling the process, it is preferred to control the introduction of dissolved oxygen into the cultivation vessel in dependence from the signal of the optical detector that forms part of the system for measuring the dissolved oxygen concentration in the matrix, preferably by calculating the dissolved oxygen concentration from the phase shift signals using a pre-determined calibration relation, which can be temperature-dependent and/or optionally be pressure-dependent. The introduction of dissolved oxygen into the cultivation vessel can e.g. be performed by regulating the dissolved oxygen concentration in cell culture medium introduced into the cultivation vessel, and/or by changing the composition of the cultivation medium.

The production process of the invention is suitable for producing a three-dimensional tissue in a three-dimensional shape predetermined by the three-dimensional shape of the matrix in which a support containing a dye is immobilized that is sensitive to dissolved oxygen. The cultivated three-dimensional tissue comprising the matrix can contain the support containing the dye, e.g. the dye-containing support is mixed into the matrix material, preferably immobilized within the matrix material.

Optionally, in the tissue comprising the matrix, the immobilization of the dye on the matrix can be dissolved, e.g. by digestion of the bonds immobilizing the dye-containing support to the matrix. When using a polymerizable compound for immobilization, e.g. fibrinogen, the resultant polymer, e.g. fibrin, can be enzymatically digested. Digestion of the coupling bond, preferably of the biodegradable polymer immobilizing the dye-containing support to the matrix can be obtained by contacting the cultivated three-dimensional tissue comprising the matrix with an enzyme hydrolysing the bonds, e.g. the polymer, or by allowing the physiological hydrolysis to occur following the implantation of the cultivated three-dimensional tissue in the body of a recipient, preferably in a human recipient.

DETAILED DESCRIPTION OF THE INVENTION

The invention is now described in greater detail by way of examples and with reference to the figures, showing in FIG. 1 a schematic overview of an apparatus suitable for carrying out the process of the invention, in FIG. 2 a micrograph of matrix containing oxygen-sensitive dye and cells after 12 days cultivation in a flow-through reactor vessel, in FIG. 3 the dissolved oxygen concentration determined from the phosphorescence emission of the dye contained in the matrix, in FIG. 4 the relative oxygen concentration within the matrix, in FIG. 5 the oxygen concentration determined during cultivation of adMSC cells in a collagen matrix, in FIG. 6 the oxygen concentration determined during cultivation of NIH-3T3 cells in a collagen matrix, and in FIG. 7 the oxygen concentration determined during cultivation of U2 OS cells in a collagen matrix.

Figure 1:
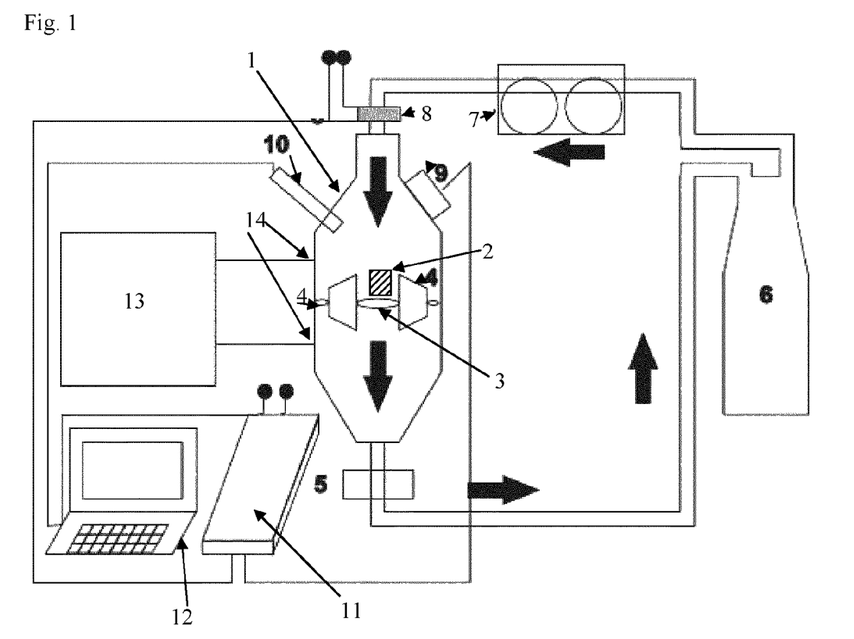

In FIG. 1, a culture vessel 1 as it is generally preferred for use in the invention is shown, having a generally funnel shaped upper section and an essentially funnel shaped lower section along a common longitudinal axis, which is preferably disposed vertically. Within the vessel 1, a porous carrier 3 is arranged, essentially horizontally, for receiving a matrix 2. As generally preferred, the cross-section of the vessel 1 between the inner vessel wall and the carrier 3 is provided with openings which allow an essentially laminar flow of medium, generally along the longitudinal axis of the vessel 1. Preferably, the cross-section of the vessel 1 between the inner vessel wall and the carrier 3 can be provided with a control mechanism to regulate the cross-section of the openings, e.g. a sectorized damper 4 like an iris. Preferably, the culture vessel 1 is provided with a medium circulation system, having an outlet at the lower end of the vessel 1 leading into a medium reservoir, and an inlet opening at the opposite end of the vessel 1 connected to an inlet line, preferably provided with a feed pump 7. The excitation light source 8, e.g. a laser, optionally an LED, is arranged to irradiate the region adjacent the carrier 3, in which the matrix 2 is arranged. As an example, the excitation light source 8 can be arranged within the longitudinal central axis of the vessel 1 above the carrier 3. The vessel 1 can have two pressure ports 14, e.g. one on each side of the carrier 3, e.g. one upstream and one downstream with respect to the carrier 3. Preferably, the pressure ports 14 are connected to a control device 13 which preferably is disposed to transmit pressure signals to a computer 12, e.g. for controlling the feed pump 7 in dependence on pressure signals transmitted from the pressure ports 14.

The optical detector 9, which can e.g. be a photomultiplier or an optical camera, is directed to the region above the carrier 3, in which region the matrix 2 is arranged in order to receive emission originating from the dye contained in the support which is immobilized in the matrix.

Preferably, the excitation light source is controlled by a control device, which can be a computer 12, preferably a sinusoidal frequency generator contained in a computer-controlled electronic control device 11 having a lock-in amplifier 11, e.g. the computer 12 and/or the computer-controlled electronic control device 11 can be disposed to control the frequency and/or wavelength generated by the excitation light source. Further, the optical detector 9 is connected to a computer 12 and/or to the sinusoidal frequency generator 11, with the computer-controlled electronic control device being disposed to control the light source 8, e.g. disposed for modulation of the irradiation to two modulated frequencies, to receive the measurement signal from the optical detector and to calculate the phosphorescence decay time from emission by the dye from the measurement signal, wherein the dye is immobilized in matrix 2. Preferably, the computer-controlled electronic control device 11 is disposed for calculating the phase shift of the emission, e.g. in correlation to modulated excitation light, preferably in correlation to at least two modulation frequencies of the excitation light, and disposed for correlating the phase shift to a dissolved oxygen concentration using a pre-determined temperature-dependent calibration curve of the dissolved oxygen concentration to the phase shift. Optionally, both the computer 12 and the computer-controlled electronic control device 11 can be contained in one computer, or computer 12 and the computer-controlled electronic control device 11 can be separate and connected.

As an example, the excitation light source 8 can be a laser and/or LED emitter of 509 nm (obtainable from Luxeon Star), optionally blocking red wavelengths by a green band pass filter. In the alternative, a green-emitting LED producing a wavelength of 532 nm with a focusing lens system could be used, or a green diode laser emitting at 510-515 nm.

A wavelength of 500-570 nm for the excitation light source is preferred, because it has been found that a blue excitation wavelength can result in the production of toxic singulett oxygen by riboflavin.

Preferably, the excitation light source is modulated to at least two frequencies, e.g. of 6 kHz and 11 kHz.

Generally preferred, the vessel is equipped with a temperature sensor 10, which can be coupled to the computer 12, and is used for the temperature control of the vessel 1. As generally preferred, the signal from the temperature sensor is used in the determination of the dissolved oxygen concentration from phase-shift determined from the phosphorescence signal, e.g. using a pre-determined calibration relation between the phase-shift and the dissolved-oxygen concentration.

For controlling the dissolved oxygen concentration within the matrix 2, the signal representing the dissolved oxygen concentration derived from the measurement signal of the optical detector 9 can be used to control the dissolved oxygen concentration in the medium introduced into the vessel 1, e.g. by controlling the dissolved oxygen concentration in the medium in a medium reservoir 6, and/or by controlling the flow rate of the medium introduced into the vessel 1, e.g. by controlling the feed pump 7.

In the examples, the oxygen-sensitive dye is represented by Pt(II)-tetra-pentafluorophenyl-porphyrin. When analysing the support containing the dye according to the following examples, it was found that the emission, namely the phase-shift of the emission detected upon irradiating the matrix with an excitation wavelength, preferably the phase-shifts determined for each modulation frequency of the excitation irradiation, was indicative of the dissolved oxygen concentration of the medium, and human cells could be cultivated to grow within these matrices containing the particulate support containing the oxygen-sensitive dye. The particulate support containing the oxygen-sensitive dye is also referred to as dye-loaded support or beads. The collagen matrix used had a mean pore size of 50-150 μm (obtainable from Mamiderm). The matrix could optionally be treated with UV and/or isopropanol and air-dried prior use and/or sterilized by γ-irradiation.

EXAMPLE 1

Immobilization of Dye on Particulate Support, and Immobilization of the Dye-Containing Support in a Matrix For immobilizing a dye on a particulate support, cross-linked polystyrene beads with diameters in the range of 50 μm were suspended in a solvent, e.g. dichloromethane, in which the dye, e.g. Pt(II)-tetra-pentafluorophenyl-porphyrin was dissolved. After filtering and washing coloured microbeads were received, which show strong oxygen-dependent phosphorescence. Optionally, even nanobeads with diameters <1 µm could be used. In this case, the dye was contacted with superficially carboxylated nanobeads of polystyrene for staining using dichloromethane, followed by filtering the suspension through glass wool and dialysis for removal of unbound dye. The dye-loaded beads had a mean diameter of 300 nm and clusters of up to 1 µm size. Optionally, for blocking free carboxylate binding sites, which is necessary in the case small nanobeads to prevent agglomeration, the beads were subsequently contacted with unspecific protein, e.g. with BSA.

For immobilizing the dye-loaded beads to a collagen matrix, the beads were contacted with fibrin glue by mixing the dye-loaded beads with fibrinogen, contacting the admixture with the swelled collagen matrix, and adding starter, e.g. thrombin. It was found that the dye-loaded beads were bound to the matrix by the fibrin polymer.

EXAMPLE 2

Production of a Three-Dimensional Tissue

As an example for animal cells, adherently growing human mesenchymal stem cells were cultivated in cell culture medium (DMEM—Ham's F12, supplemented with 5% fetal calf serum, antibiotics, sodium pyruvate and non essential amino acids) at 1 to $2 \times 10^7$ cells. Alternatively, cells were U2-OS (osteosarcoma cells) or NIH-3T3-cells, cultivated in DMEM-high glucose medium supplemented with 5% FCS and sodium pyruvate, or primary human adherently growing mesenchymal stem cells (adMSC).

The matrix could be cut to a sheet of 3-5 mm thickness with a width of 1 cm and a length of 9-10 cm. Preferably, micro beads containing dye were applied to one side of the strip-shaped matrix, i.e. immobilized onto the matrix by mechanical entrapment, seeded with the cells and rolled into a cylinder, and then placed on the carrier that was arranged within the vessel 1 of a bioreactor system as generally shown in FIG. 1.

In the alternative to immobilizing the dye-loaded beads by polymerised fibrinogen, the dye-loaded beads could be contacted with the matrix material prior to seeding the cells, followed by folding of the matrix to mechanically entrap the dye-loaded beads.

For cultivation in the bioreactor vessel, cell culture medium with high glucose, supplemented with 0.01 M HEPES was used at 37° C. and 5% $CO_2$. with continuous pumping of medium through the vessel at a rate known to establish laminar flow about the matrix.

Figure 2:
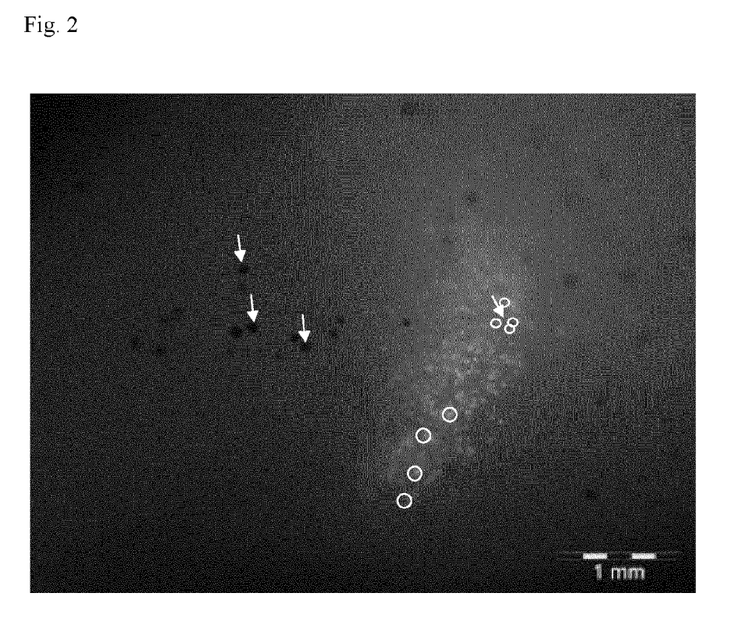

Analysis by staining with fluorescein diacetate at 2.4 mM in microscopic analysis showed that cells seeded onto the matrix were viable. FIG. 2 shows a micrograph of the collagen matrix containing micro beads (indicated by white arrows) with adherently growing cells (encircled), following 12 days of cultivation in the vessel.

The dissolved oxygen concentration was optically measured a 540 nm excitation light source (LED), and detecting the phase shift under sinusoidal modulation of the excitation light at two modulation frequencies, i.e. at 3 kHz and 11 kHz. From the phase shift as determined by correlating the excitation frequencies with the detected emission, the decay time of the phosphorescence was calculated, from which subsequently the dissolved oxygen concentration was determined by correlating the phase shifts with a pre-determined calibration curve generated with the same matrix containing the oxygen-sensitive dye-loaded support but without cells, equilibrated with medium of different known oxygen concentrations.

Figure 3:
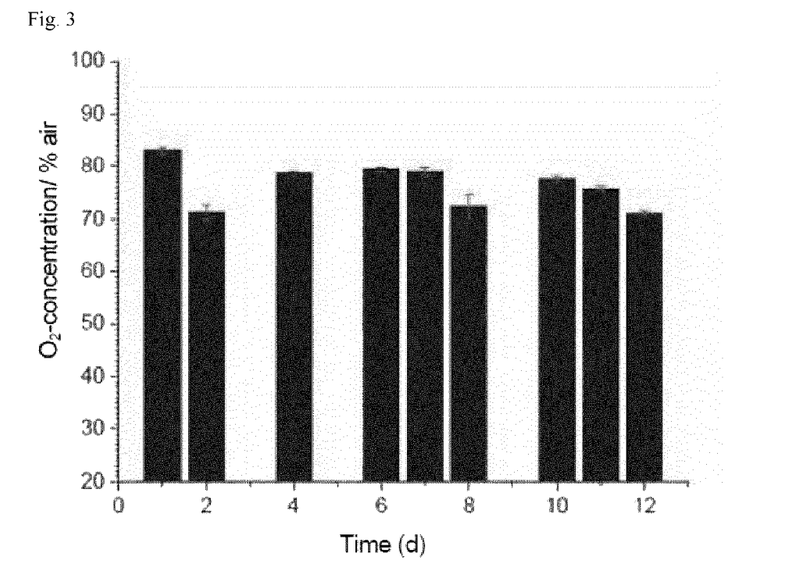

In FIG. 3, the result of the measurement under constant cultivation conditions (1 mL/min) flow rate of medium, shows that over the cultivation time, the measurement signal shown as relative concentration (100% equals equilibrium to air) decreases over the cultivation time. In this experiment, new dye loaded beads were added to the matrix at days 4 and 10. It is assumed that the decrease in the measurement signal is due to washing out of beads from the matrix.

When measuring the signal intensity in dependence on the position of dye loaded polymer beads immobilized within the matrix, it was found that a suitable signal for measuring the dissolved oxygen concentration could be obtained for dye-loaded support located up to 5 mm, preferably up to 10 mm, and more preferably up to 12 mm within the inner volume of the matrix.

Figure 4:
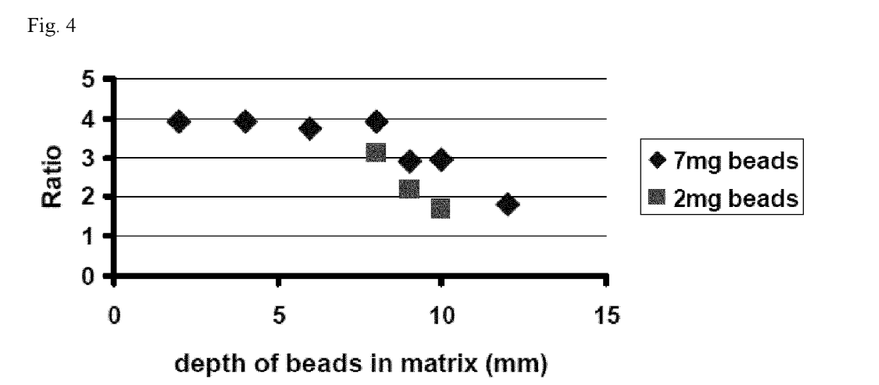

FIG. 4 shows the result of the measurement of the emission signal detected from a collagen matrix containing the beads at various positions from the outer surface of the matrix, i.e. for varying depths of the beads in the inner volume of the matrix. For this test, a total of 2 or 7 mg dye-loaded beads (support) were used and it was found that the value indicating the dissolved oxygen concentration that was derived from the measurement signal of the optical detector decreased with increasing depths of the beads within the matrix, and it was found that a suitable signal could be found for a position of approximately 7-8 mm from the outer surface of the matrix, i.e. from a depth of at least 7-8 mm within the matrix, and even up to at least approximately 10-12 mm within the matrix. This shows that the method of the invention allows the determination of the dissolved oxygen concentration also within the inner volume of the matrix.

When using fixation of the dye-loaded beads to the matrix by generating fibrin polymer from fibrinogen in a mixture of the dye-loaded beads in contact with the matrix by adding thrombin as a starter compound, it could be seen that the measurement signal for the dissolved oxygen concentration derived from the measurement signal of the optical detector was more constant, indicating that the mobilisation of beads within the matrix was significantly reduced by the immobilization of the beads to the matrix by the bio-degradable fibrin polymer.

Figure 5:
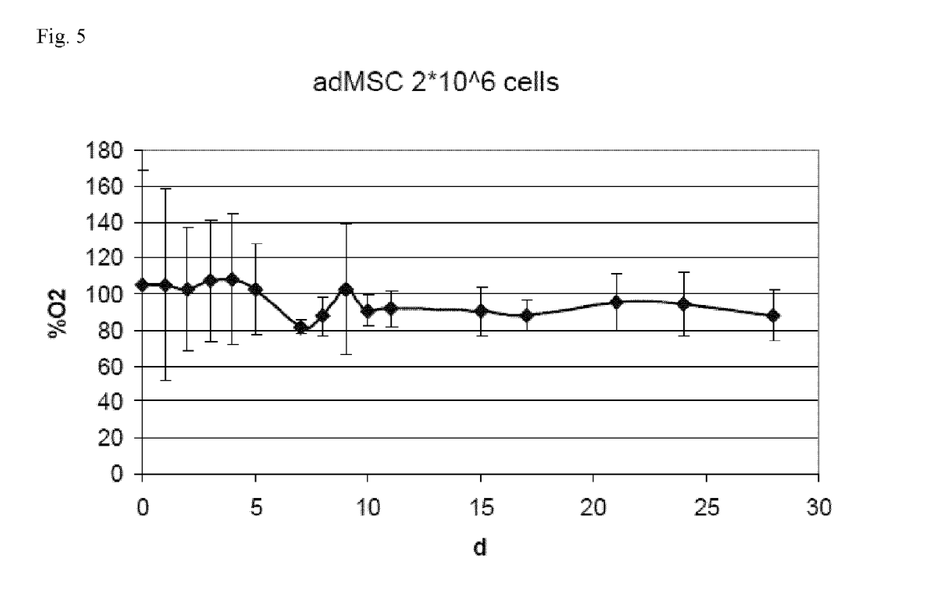
Figure 6:
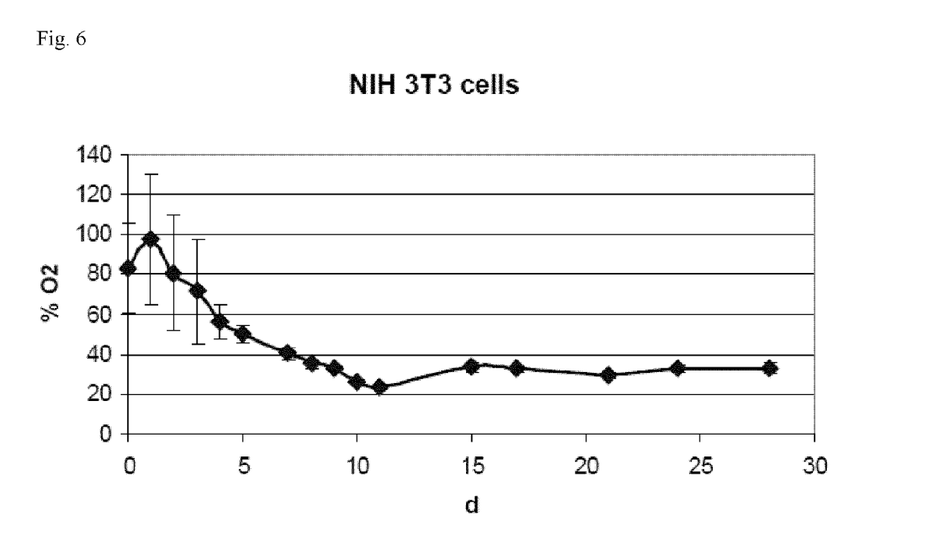
Figure 7:
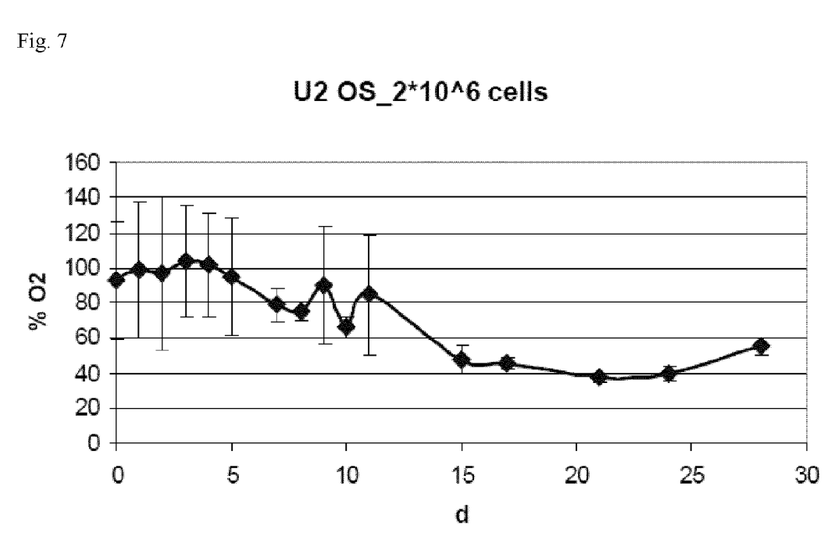

FIGS. 5 to 7 show the dissolved oxygen concentration determined from the phase-shift of phosphorescence from Pt(II)-tetra-pentafluorophenyl-porphyrin contained in polystyrene beads as a support, which was contained in interstices in a collagen matrix cultivated with adMSC, NIH-3T3 cells, and US-OS cells, respectively.

The invention claimed is:

1. Process for producing a three-dimensional tissue by introducing eukaryotic cells into a matrix and cultivating the cells within the matrix in a cell culture medium within a cell culture vessel while determining the dissolved oxygen concentration by measuring the emission from an oxygen-sensitive dye which is phosphorescing upon irradiation of an excitation wavelength, the process comprising integrating a support into the matrix, the support being particulate and permeable for oxygen and containing in its inner volume the oxygen-sensitive dye, directing an irradiation onto the matrix, the irradiation having an excitation wavelength suitable for exciting emission from the oxygen-sensitive dye, wherein the irradiation having the excitation wavelength is intensity-modulated to at least two frequencies, measuring the emission from the support containing the oxygen-sensitive dye, and detecting the time-resolved intensity of radiation emitted by the dye, wherein the phase-shift of the emission is determined from the emission for each of the at least two frequencies and determining the decay time of the phosphorescence of the oxygen-sensitive dye from the phase-shift, and wherein the irradiation and emission are selected and the matrix is configured such that the irradiation and emission at least partially cross a volume portion of the matrix to measure at a depth of at least 5-12 mm in the matrix.

2. Process according to claim 1, wherein the support containing the oxygen-sensitive dye is immobilized in the inner volume of the matrix by arrangement of the support in interstices of the matrix.

3. Process according to claim 2, wherein the support is coupled to the matrix by polymerization of polymerizable compounds in the presence of the support containing the oxygen-sensitive dye in contact with the matrix.

4. Process according claim 1, wherein the oxygen concentration of the medium is controlled in dependence from the measurement signal of the emission from the oxygen-sensitive dye.

5. Process according to claim 1, wherein the emission is determined in a pre-set frequency range using a lock-in amplifier.

6. Process according to claim 1, wherein during cultivation, the matrix is arranged on a porous carrier and the cell culture medium is pumped in a laminar flow adjacent the matrix.

7. Process according to claim 1, wherein the oxygen concentration is determined from the emission from the support containing the oxygen-sensitive dye using a pre-determined calibration curve of the correlation between the emission and the oxygen concentration.

8. Process according to claim 7, wherein the calibration curve is pre-determined at the cultivation temperature to which the vessel is controlled, and/or the calibration curve is pre-determined at a pressure at which the cells are cultivated within the matrix.

9. Process according to claim 1, comprising continuously introducing cell culture medium into the vessel and withdrawing cell culture medium from the vessel and circulating at least a fraction of the cell culture medium to the vessel.

10. Process according to claim 1, wherein the support is selected from the group consisting of polystyrene, polymethylmethacrylate, polyethylene, polypropylene, ormosile, silicone, sol-gel matrices, compounds having a dendrimer structure, blends of these polymers and/or of their halogenated derivatives and mixtures thereof.

11. Process according to claim 1, wherein both the light source irradiating the excitation wavelength and the detector receiving the emission from the dye are arranged within the wall of the cultivation vessel.

12. Process according to claim 11, wherein the light source and the detector are flush with the inner surface of the cultivation vessel.

13. Process according to claim 2, wherein the support containing the oxygen-sensitive dye is in an admixture with a polymerizable compound in contact with the matrix.

14. Process according to claim 7, wherein oxygen concentration is determined with correlation to the temperature of the medium within the vessel and with correlation to the pressure within the vessel, using the temperature-dependent signal of a temperature sensor and a pressure-dependent signal at one or two pressure-ports arranged in the vessel.

* * * * *